United States Patent [19]

Sommermeyer et al.

[11] Patent Number: 4,849,408

[45] Date of Patent: Jul. 18, 1989

[54] METHOD OF TREATMENT OF CEREBRAL DISTURBANCES WITH OLIGOPEPTIDES CONTAINING TRYPTOPHAN

[75] Inventors: Klaus Sommermeyer; Burghard Weidler, both of Rosbach, Fed. Rep. of Germany

[73] Assignee: (501) Fresenius AG, Bad Homburg, Fed. Rep. of Germany

[21] Appl. No.: 1,517

[22] Filed: Jan. 7, 1987

[30] Foreign Application Priority Data

Jan. 18, 1986 [DE] Fed. Rep. of Germany ....... 3601398

[51] Int. Cl.$^4$ .............................................. A61K 37/02
[52] U.S. Cl. ........................................ 514/18; 514/19; 548/496
[58] Field of Search ............... 530/328, 329, 330, 331; 260/998.2; 514/17, 18, 19, 415, 803, 814

[56] References Cited

U.S. PATENT DOCUMENTS

| 3,842,064 | 10/1974 | Greuen et al. | 530/330 |
| 4,085,207 | 4/1978 | Aoki et al. | 514/415 |
| 4,110,438 | 8/1978 | Gahwyler | 514/15 |
| 4,340,592 | 7/1982 | Adibi | 514/19 |
| 4,405,629 | 9/1983 | Wurtman | 514/415 |
| 4,551,471 | 11/1985 | De Luca et al. | 514/419 |
| 4,567,162 | 1/1986 | de Castiglione et al. | 530/329 |
| 4,687,763 | 8/1987 | Wurtman | 514/415 |

Primary Examiner—Delbert R. Phillips
Assistant Examiner—T. D. Wessendorf
Attorney, Agent, or Firm—Omri M. Behr

[57] ABSTRACT

The use of tryptophan containing oligopeptides for the treatment of cerebral disturbances in particular sleeplessness and depression is disclosed. The use of glycyl tryptophan, if desired, in combination with tryptophan itself, is especially preferred.

8 Claims, 1 Drawing Sheet

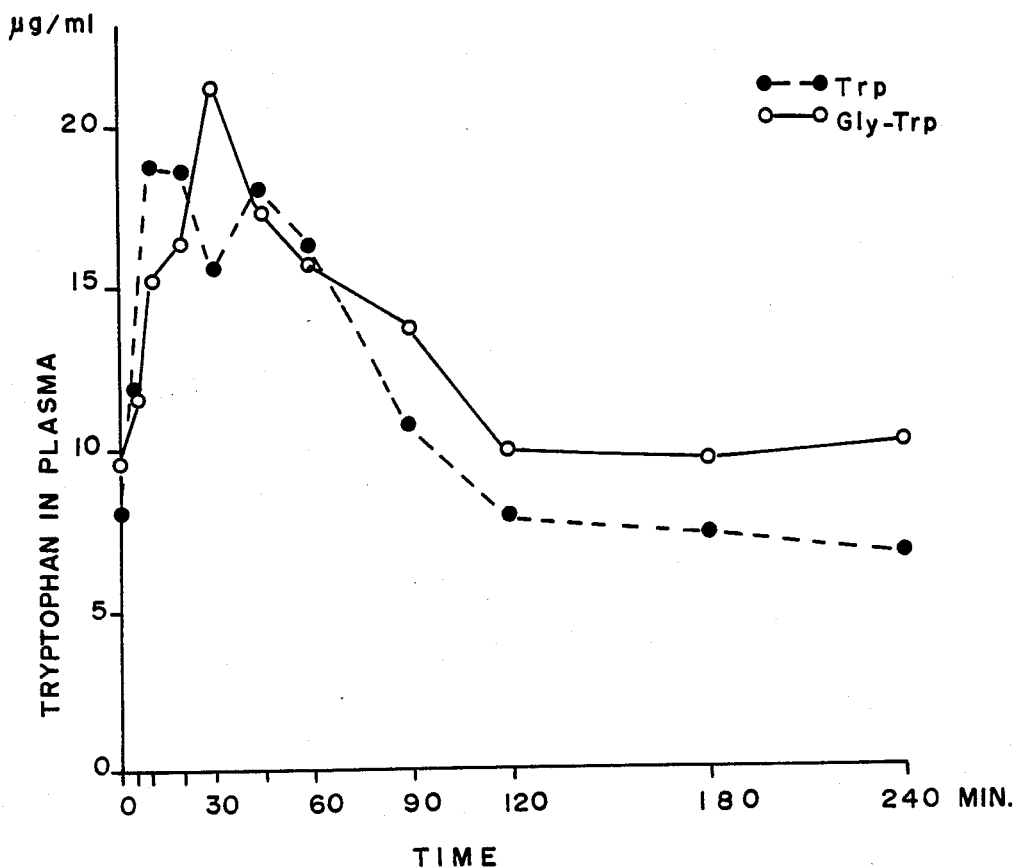

METHOD OF TREATMENT OF CEREBRAL DISTURBANCES WITH OLIGOPEPTIDES CONTAINING TRYPTOPHAN

BACKGROUND OF THE INVENTION

Sleeplessness and depression are well known problems which are suffered daily by countless people. A vast compendium of reliable and effective pharmacologically active agents are known to treat these conditions. However, in view of their various side effects, they cannot be utilized without some care and thought. Where it is necessary to treat these conditions on a long term basis, care must be taken to avoid setting up dependencies, particularly where benzodiazepines are involved. It should be noted that barbiturates and other well accepted sleeping aids can lead to dependence, pose a risk of being utilized for suicidal purposes and have a plurality of side effects.

Recently, studies on the physiology of sleep have revealed various results confirming the complexity of the sleep termination and also the complex nature of the physiological and biochemical mechanisms which are responsible for the interruption of sleep and which insure the regular progression of the various phases of sleep.

Different portions of the brain take part in such mechanisms and are influenced by various transfer compounds i.e. neurotransmitters, which consist principally of amino acids.

The best known of such neuro transmitters are Noradrenalin and Dopamine (synthesized from Tyrosin and Serotonin which is synthesized from Tryptophan).

Studies have shown that low levels of particular neurotransmitters or their precursors can influence conditions of excitation which in turn often lead to psychic illnesses, for example disturbed sleep or depression. Sleep is, induced through Serotonic neurons in the so-called Raphe system in the border regions between the middle and rhombic brain. If the biosynthesis of serotonin from tryptophan is blocked in the brain, sleeplessness will occur. Lack of serotonin cannot be relieved by direct substitution since serotonin, quite apart from undesired side effects, cannot pass through the blood/-brain barrier by itself. Thus, the required amino acid tryptophan must be produced in these serotonergic neurons. This synthesis takes place in two steps wherein first 5-hydroxy tryptophan is formed by the action of trytophan hydroxylase, which is then decarboxylated by aromatic aminoacid decarboxylase to yield 5-hydroxy tryptamine, that is to say serotonin.

Thus a lack of tryptophan gives rise to disturbances of sleep and depressions. Tryptophan insuffiency and its effects were therefore successfully treated by administration of free tryptophan which can indeed pass through the blood/brain barrier. Such a treatment has certain advantages vis a vis the classical antidepressants which block the inactivation of central transfer agents such as serotonin and the conventional hypnotics which unspecifically dampen the activating formatio reticolaris. The advantage of this therapy is that it is direct and free from side effects since it does not lead to dependency or addiction. It does not give rise to the risk of being a suicidal agent and furthermore gives the posibility, in cases of severe disturbance, of enabling a reduction of the required dosage of active pyschopharmaceutical agents by the administration of tryptophan (see Der Deutsche Apotheker) (The German Pharmacist) 35 #4 1-7(1983)).

The problem with the administration of tryptophan which can only pass the blood/brain barrier in its free form lies in the relatively low levels of resorption, that is to say, resorbability of the tryptophan from the gastrointestinal tract and the rather limited transportation of tryptophan through tissue membranes so that tryptophan must be administered in higher doses and with greater dosage frequency than is desirable. In order to treat cerebral disturbances it is desirable to maintain a high level of serotonin in the brain and a low level in the blood, since otherwise a high serotonin level in the blood can lead to peripheral disturbances.

Heretofore, attempts have been made to utilize the serotonin precursor 5-hydroxy tryptophan in place of serotonin or tryptophan. The problem with this approach is that 5-hydroxy tryptophan is readily changed by decarboxylase in the blood into serotonin so the concentration of serotonin in the blood rises to undesirable levels.

It has also been observed that there are certain undesirable intestinal side effects, for example, nausea and diarrhea. In order to avoid such side effects the 5-hydroxy tryptophan must be administered together with a decarboxylase blocking agent such as Benserozide (INN) that is to say N-(DL)-seryl N'-(2,3,4-trihydroxy benzyl) hydrazine or Carbidopa (INN) that is to say (−)-L-alphahydrazinyl-3,4-dihydroxy-alpha methyl hydroxycinnamic acid. These decarboxylase blockers however have the disadvantage that they also give rise to undesired and occasionally substantially bothersome side effects.

It is therefore still desirable to provide suitable materials for the therapy of cerebral disturbances in particular sleeplessness and depression. The task of the present invention therefore was to provide a new agent for the treatment of cerebral disturbances such as sleeplessness and depression which does not have the disadvantages of the known agents, which does not require the use of decarboxylase blockers, is not a toxic and has substantially no side effects, does not lead to dependence or addiction, carries no suicide agent risk with it and is readily resorbed by the body, that is to say smaller dosage amounts are required and good transport through tissue membranes is achieved.

SUMMARY OF THE INVENTION

It has found that the use of certain oligopeptides which have combined therein tryptophan and at least one other amino acid or an amino acid derived from tryptophan for the treatment of cerebral disturbances in particular sleeplessness and depression as well as pharmaceutical preparations for the handling thereof which contain such oligopeptides or mixtures of such oligopeptides.

It has been our surprising finding that such materials are effective either per se or when administered in conjunction with tryptophan. The oligopeptides of the present invention comprise a combination of not more than a total of ten amino acids preferrably nine amino acids of which at least one is L-tryptophan or a derivative thereof.

DESCRIPTION OF THE PREFERRED EMBODIMENTS

It should be noted herein that in accordance with current convention, all naturally occurring amino acids are considered to exist in the L-form therefore where no prefix occurs, the L-form is assumed.

The nomenclature utilized is that specified by the IUPAC-IUB Commission on Biochemical Nomenclature (European J. Biochem.) (1984), 138 9–37).

Further in a oligopeptide, unless otherwise signified, the left hand member of the chain has a free amino group and the right hand member a free carboxy group.

The oligopeptides which it is preferred to utilize in the present invention have the formula:

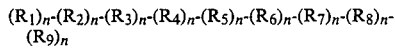

wherein n is 1 or 0 and $R_1$ through $R_9$ is an amino acid. The amino acids $R_1$ through $R_9$ may be the same or different provided that at least one member of the group is tryptophan or a derivative thereof suitably 5-hydroxy tryptophan. It is especially preferred that there be between 2 and 5 amino acids in the peptide chain other than tryptophan and 5-hydroxy tryptophan. Amino acids may be selected from the group consisting of Gly, Ala, Ser, Thr, Cys, Met, Asp, Glu, Phe, His, Lys, Pro, Tyr, Val, Iso, and Leu, preferably Gly, Ala, Ser, Thr, Cys, Met, Asn, Asp, Glu, Gln, His, Lys, and Pro especially Gly.

The invention is not limited to the use of a single oligopeptide, mixtures of the oligopeptides with each other or with tryptophan or tryptophan derivatives may be employed. Equally, there may be employed the addition salts thereof with pharmaceutically acceptable acids or bases such as for example with hydrochloric or acetic acid, the latter being preferred.

Especially as suitable as oligopeptides are, Trp-Trp, Ala-Trp, Trp-Ala, Gly-Trp, Trp-Gly, 5-OH-Trp-Gly, 5-OH-Trp-Ala, Gly-5-OH-Trp, Ala-5-OH-Trp, Trp-Trp-Trp, Ala-Gly-Trp, Trp-Ala-Gly, Ala-Trp-Gly, Gly-Trp-Ala, Ser-Trp-Ala-Trp, Ser-Trp-Ala-Gly, Ser-Trp-Ala-Trp-Gly, and Trp-Ser-Ala-Gly-Trp.

As preferred peptides there may be mentioned Trp-Trp, Ala-Trp, Trp-Ala, Gly-Trp, Trp-Gly, 5OH-Trp-Gly, 5-OH-Trp-Ala, Gly-5-OH-Trp, Ala-5-OH-Trp, Trp-Trp-Trp, Ala-Gly-Trp, Trp-Ala-Gly, Ala-Trp-Gly, Gly-Trp-Ala and Ser-Trp-Ala-Trp, especially preferred for the purposes of this invention are Trp-Trp, Ala-Trp, Trp-Ala, Gly-Trp, Trp-Gly and most especially preferred is Gly-Trp.

The oligopeptides utilized in the present invention are synthesized in the conventional manner including, for example, the so-called genetic methods. In place of utilizing the purified peptides, or mixtures thereof, the hydrolysate which contains these oligopeptides may also be utilized. The preferred method is the Merrifield method wherein a terminal amino acid, suitably the carboxy terminal acid is protected at the amino moiety and coupled to a substrate having, suitably, a labile amino moiety. The terminal amino group is deprotected and the synthesis continued until the desired oligopeptide is obtained and cleaved.

Especially preferred is a mixture of tryptophan and glycyl-tryptophan. The pharmaceutically acceptable acids and bases which may be used in conjunction with the oligopeptides to form the salts thereof include but are not limited to acetic or malic acids. Amino acids salts such as lysinates, argininates and ornithinates may be employed.

When utilized in combination with tryptophan, the oligopeptide/tryptophan weight/weight ratio lies between 1:10 through 10:1, preferably between 1:5 to 5:1 especially 1:2 to 2:1 and most preferred is the ratio of 1:1. The oligopeptides of the present invention provide substantial advantages in the treatment of sleep disturbance and depression vis a vis conventional agents for this purpose. They are not toxic, they have no side effects, they do not lead to dependency or addiction, they do not have the possibility of being utilized as suicide agents, they are readily absorbed by the body and show a superior pharmaookinetic behavior and better transport through tissue membranes than tryptophan itself and make it unnecessary to utilize decarboxylase blocking agents. Thus, it is possible to utilize these agents in rather smaller amounts and lower concentrations. Surprisingly, it has been further found that the mixture of tryptophan with the named oligopeptides leads to excellent results in the treatment of cerebral disturbances such as sleeplessness and depression. The advantages of the present invention have been confirmed by experimental results.

The compositions utilized in the present invention, that is to say the oligopeptides or the combination of the oligopeptides with tryptophan or its derivatives, can be so formulated that they may be utilized for oral administration. For this purpose they may be mixed with conventional diluents and formulated into conventional modes or administration such as capsules, suspensions, emulsions, dispersible powders, syrups, or elixers.

The oligopeptides or their combination with tryptophan are relatively water insoluble but they may be suspended in sorbitol or glycerine solutions containing a high percentage of water provided a sufficient amount of emulsifier or suspending agent is added thereto. If is desired flavorants or colorants may also be added.

Fluid or solid formulations can be put up in capsules for oral administration. The active constituents may also be suspended or dissolved in animal or vegetable oils such as sunflower oil, soy oil, corn oil, or cod liver oil. Conventional additives for example anti oxidants may also be employed.

Solid formulations for use in capsules may be put up with the usual carrier material. Tablets may also be formulated in the conventional manner, as inert diluents or carriers there may be utilized magnesium carbonate or lactose in combination with the usual disintegrants for example corn starch or alginic acid and or smoothing materials for example magnesium stearate.

It is preferred to administer (to humans of ca 60–70 Kg body weight) from 1–10 g/day of tryptophan content, suitably 1.5–3 g/day thereof.

EXAMPLE I

Synthesis of Boc-trytophan tryptophan sulfate (2.28 g, 10 mmole) was suspended in water (10 ml) and triethylamine (2.8 ml, 20 mmole) was added. Thereafter the solution thus obtained was diluted with dioxan (10 ml) and di-tert-butyl dicarbonate (2.4 ml, 10 mmole) added to the mixture with stirring on ice bath (cooling on ice). The mixture was then allowed to warm to ambient temperature. After 5 hours, second portions of triethylamine (1.4 ml, 10 mmole) and di-tert-butyl dicarbonate (1.2 ml. 5 mmole) were added while stirring was continued at ambient temperature overnight. The mixture was filtered and evaporated under reduced pressure. The residue was dissolved in chloroform (50 ml), the solution was dried over sodium sulfate and concentrated under reduced pressure to an oil which was crystallized from chloroform/acetone. Boc-tryptophan separated as a triethyl-amine-sulfate-salt.

EXAMPLE II

Coupling of Boc-trytophan to Support Phase [SP]

3.11 g (7 mM) Boc-tryptophan in 50 ml DMF was reacted with 1.89 g (14 mM) HOBt and 1.1 ml (7 mM) DIC at room temperature for 30 minutes, and the resulted active ester solution in this way was added to aminomethyl resin [SP] in 5 g. dichloro-methane, deprotonated in 10% diisopropyl ethylamine chloroform mixture and washed twice with DMF. The reaction was complete for 90 minutes, tested by ninhydrin-reaction. Finally, the coupled resin was washed with DMF, dichloromethane and DMF again.

EXAMPLE III

The synthesis of an oligopeptide of the formula H-$Asp_1$-$Ser_2$-$Tyr_3$-$Arg_4$-$Lys_5$-$Trp_6$ was carried out in a stepwise manner on a Beckman 990 synthesiser starting with the appropriate Boc-Trp-[SP] in accordance with the procedures set forth below.

(a) deblocking and build-up.

Deblocking is carried out in accordance with Schedule A as follows:

| SCHEDULE A | |
|---|---|
| Reagent | Mixing Time (mins) |
| 1. TFA/Toluene 1:2 * | 2 |
| 2. TFA/Toluene 1:2 * | 28 |
| 3. $CH_2Cl_2$ | 2 |
| 4. MeOH | 2 |
| 5. $CH_2Cl_2$ | 2 & 2 |
| 6. DIEA (10%) in $CH_2Cl_2$ | 2 & 8 |
| 7. MeOH | 2 |
| 8. $CH_2Cl_2$ | 2 |

Coupling is carried out in accordance with Schedule B as follows:

| SCHEDULE B | |
|---|---|
| Reagent | Mixing Time (mins) |
| 9A. DIC (2 eq) + HOBt (4 eq) | — |
| 10A. Bcc Amino Acid (2 eq) + HOBt (2 eq) # | 60-90 |
| or | |
| 9B. DIC (2 eq) + | — |
| 10A. Bcc Amino Acid (4 eq) @ | 60-90 |
| 11A. DMF | 2 |
| or | |
| 11B. $CH_2Cl_2$ | 2 |
| 12. $CH_2Cl_2$ | 2 & 2 | prepared 30 minutes previously in DMF, mixing 9A & 10A@ prepared 30 minutes previously in $CH_2Cl_2$, mixing 9B & 10A Briefly, 1 to 2 mmol. of Boc-protected amino acid in DMF is used per gram of resin. When Boc-Arg (Tos) is being coupled, a mixture of 50% DMF and methylene chloride is used. Bzl ether is used as the hydroxyl side-chain protecting group for Ser and Thr. 2-Chloro benzyloxycarbonyl (2Cl-Cbz) is used as the protecting group for the Lys side chain. Tos is used to protect the guanidino group of Arg and the Glu and Asp side-chain carboxyl group is protected with OBzl or OOhx. The phenolic hydroxyl group of Tyr is protected with 2,6-dichlorobenzyl (DCB).

The following compound is obtained:

Boc-$Asp_1(X^1)$-$Ser_2(X^2)$-$Tyr_3(X^3)$-$Arg_4(X^4)$-$Lys_5(X^5)$-Trp-[SP]

wherein $X^1$ is O— cyclohexylester, $X^2$ is O-benzyl ether, $X^3$ is O-2,6-ClBz ether, $X^4$ is tosyl, $X^5$ is 2-Cbz, (b) Cleavage and deprotection (The procedure followed is substantially that of Tam et al J. Amer. Chem. Soc. 105, 6442, (1983))

The protected peptide produced as above is utilized as starting material.

The protected peptide is treated with 50% TFA-Toluene (1:2 v/v) prior to the HF treatment using two treatments with 50% TFA in $CH_2Cl_2$ (2×28 min. then washed 3X with $CH_2Cl_2$).

The incomplete mixing of the HF reagent and the peptidyl resin or peptide can be alleviated simply by using the following order of addition of the reagents: (a) peptide or peptidyl-resin, (b) p-cresol, p-thiocresol, or both, in a melted form, carefully on top of the resin by a warm peptide, (c) after cooling and the p-cresol mixture has solidified, magnetic stirring bar, and (d) dimethyl sulfide.

(a) Low Concentration HF Step.

The reagents (dimethyl) sulfide, 6,5 ml.; p-cresol, 0.75 ml.; p-thiocresol, 0.25 ml.), total volume 7,5 ml, and peptide-resin (1.0 g.) were placed in the reaction vessel and connected to the HF line. The vessel was cooled to −78° C. for 0.5 hours (longer cooling time for large volume of reagent). The line was evacuated briefly for 0.5 min. and HF was quickly distilled into the evacuated reaction vessel to a 10 ml mark (or any desired volume). The reaction was then quickly equilibrated to 0° C. by ice bath and allowed to stir vigorously for 2 hours (check stirring constantly). The HF-dimethyl sulfide-p-cresol mixture at this point was colorless to light yellow. After 2 hours, the mixture was then evacuated first with water aspirator (caution: bumping) with the valve of the reaction to the aspirator only partially opened. After most of the reagent was removed, the mixture was further evacuated by mechanical pump to a light colored liquid (usually at about 0.5 ml mark).

(b) High Concentration HF Step

The evaporated reaction vessel from the previous low concentration step, was cooled again to −78° C., evacuated, and charged again with HF to the 10 ml volume mark. [Note: if the removal of HF and dimethyl sulfide after the first stage was incomplete, recharging HF to 5 ml will result in a final HF concentration that is less than 90%. Under such circumstances the more acid-resistant resins, such as benzhydrylamine-resin, or peptides with many acid-resistant protecting groups, such as tosyl or 2,6-dichlorobenzyl, will not be completely deprotected. If there is doubt about the completion of the evaporation step, HF should be charged to 7.5 or 10 ml total volume, so that the final HF concentration will be certain to reach at least 90% by volume. A final mixture of 95% HF and 5% cresol plus thiocresol has been found to be entirely satisfactory.] The reaction was then equilibrated to 0° C. and allowed to react for 45–60 minutes. The HF was then removed as described previously.

After the cleavage process the remaining solid mass was mixed with ether several times to remove the apolar additives and apolar side products together with the contaminated traces of HF. The crude peptides were extracted from bedside the resin particles with 10% of acetic acid water mixture, then lyophilized.

The crude peptides were purified by HPLC method using semipreparative or preparative reverse-phase chromatographic columns, (Vydac C18, 10×250 mm, particle size 5 micron or Dynamax C18 Macro HPLC column 21, 4×250 mm, particle size 12 micron).
Pumps: Beckman 114M Solvent Delivery Module
Detector: Beckman 160A Absorbance Detector
Gradient Controller: Beckman 420 Grad. Cont.
Injector: Altex 210A
Detection Wavelength: 214 mm
Eluents:

A, 0.1% TFA in water (high purity)
B, 0.1% TFA in water-acetonitil ® 3:7 (by vol.) mixture.

EXAMPLE IV

Chloroformic cyanotert. butyl ester

Chloroformic cyanotert. butyl ester is prepared by reacting cyanotert butanol (10 g, 100 mMole) and pyridine (10 g, 125 mmole) in dichloromethane (150 ml) at about −40° C. together with liquid phosgene (−70° C., 40 ml, 600 mMole). The mixture is allowed to warm to room temperature and stirred over night. It is then extracted with ice cold aqueous hydrochloric acid (1N) washed twice with ice water immediately dried by shaking several times with fresh anhydrous sodium sulfate, the aqueous phases and the sodium sulfate are twice reextracted with a small amount of dichloromethane, and the combined organic phases are evaporated under reduced pressure (20° C. bath) to yield the product (17 g, 100% yield).

EXAMPLE V

N-Cyanotert-Butyloxcarbonyl-Glycine (CyOC-Gly-OH)

The crude ester produced as above is taken up into tetrahydrofuran (100 ml) and is added dropwise over about 15 minute to an ice cooled solution of Glycine (15 g, 200 mmole) in aqueous sodium hydroxide (1N, 200 ml). After stirring for one hour at ambient temperature the reaction mixture has a pH value of about 8. The pH is reduced to about 4 to 5 by the addition of aqueous sulfuric acid (2N). The solvent removed under reduced pressure and the residue extracted with a mixture of ethyl acetate/water until everything has dissolved, the aqueous phase removed, acidified to pH 1.5 to 2 and further extracted twice with ethyl acetate. The combined organic extracts are washed free of sulfate with water, dried over anhydrous sodium sulfate and the solvent removed under reduced pressure. The residue is recrystallized out of ether/petroleum ether to yield the product (16.5 g, 82%) having, after drying under vacuum, m.p. 147° to 148.5° C.

EXAMPLE VI

N-Cyanotert-Butyloxycarbonyl-Glycyl-L-Tryptophan (CyOC-Gly-Trp-OH)

1 g, 5 m mole N-Cyanotert-butyloxcarbonyl-glycine (CyOC-Gly-OH) (as prepared above) are taken up in tetrahydrofuran (30 ml) and stirred over night with dicyclohexylcarbodiimide (1.5 g, 5 mMole) and N-hydroxysuccinimide (6 mg, 5 mMole) at 0° C. The thus produced N,N'-dicyclohexyl urea is removed by filtration and the filtrate evaporated under reduced pressure. The crystalline residue, CyOC-Gly-OSU is uitlized without further purification or characterization. It is taken up in dimethyl formamide (50 ml) with tryptophan (1.02 g, 5 mmole) and N-methylmorpholine (1 g, 10 mMole) and stirred at 0° C. until all the tryptophan has dissolved (about three to four hours). The reaction mixture is allowed to stand over night in a refrigerator, treated with potassium hydrogen sulfate (1,4 g, 10 mMole) in water (20 ml) and the solvent removed under reduced pressure. The residue is worked up in the usual manner (partition between ethyl acetate and water, washing, and drying the ethyl acetate phase. After evaporation of the ethyl acetate phase there is obtained a quantative yield (2.5 g) of a viscous oil which is dissolved in ethyl acetate/ether and treated with dicyclohexylamine (900 mg, 5 mmole) to yield the product as the dicyclohexylamine salt (amorphous powder) (2.5 g, 85%).

EXAMPLE VII

Glycyl-L-Tryptophan (H-Gly-Trp-OH)

CyOC-Gly-Trp-OH-DCHA salt (200 mg, 0.35 mMole) prepared as above is taken up in an aqueous solution of calcium carbonate (150 mg, 3 ml water) and allowed to stand for 6 hours at ambient temperatures. At the end of this time thin layer chromatography shows no N-protected peptide, (elution with butanol/glacial acetic acid/water 3:1:1). The pale yellow solution is brought to pH 5 by addition of Dowex 50 (H+form) resin filtered from the ion exchanger and the solvent is removed under reduced pressure. The residue is treated with a small amount of methanol/ether.

The solvent removed under reduced pressure to yield glycyl-L-tryptophan (85 mg, 905).

In accordance with the foregoing procedure, but utilizing other amino acids moieties there may be produced any of the oligopeptides listed hereinabove.

Where it is desired however to produce oligopeptides having three or more units in the chain, it is more convenient to utilize the Merrifield procedure, an example of which is set forth above in Examples I–III. It will be understood that while this procedure is set forth for a particular peptide it is equally applicable to synthesis of all of the oligopeptides disclosed hereinabove taking account of the special procedures which are set forth hereinabove.

EXAMPLE VIII

| TABLET FORMULATION | |
|---|---|
| Group A | |
| Ala-Trp (Mp. 293–294° C., [α]$_D^{20}$ + 15.5 ± 0.5°) | 1500 Parts |
| Corn Starch | 60 Parts |
| Polyvinylpyrrolidone | 100 Parts |
| Polyvinylpolypyrrolidone | 30 Parts |
| Highly dispersed Silicon Oxide | 2 Parts |
| Isopropanol | 750 Parts |
| Water | 210 Parts |
| Group B | |
| Highly dispersed Silicon Oxide | 2 Parts |
| Magnesium Stearate | 30 Parts |
| Talc | 30 Parts |
| Polyvinylpolypyrrolidone | 30 Parts |
| Corn Starch | 250 Parts |

The Group A materials are mixed and worked into a granulated material. This granulate is caused to pass through a mesh of 1.5 mm width.

The Group B components are added thereto and the resulting mixture is pressed into tablets.

EXAMPLE IX

Tableting Composition

Ala-Trp (1500 Parts), Corn Flour (100 Parts), Alginic Acid (10 Parts) were mixed with a aqueous corn starch paste (15%-all parts by weight) worked and granulated. The granulate was passed through a mesh of 1.5 mm opening and dried at approximately 60° C. The granulate is received through a sieve of the same dimensions and the material passing through mixed with magnesium stearate (10 parts). The thus produced mixture is utilized as a tableting composition for tablets for oral administration.

EXAMPLE X

Aqueous Suspension

| | |
|---|---|
| Gly-Trp (Mp. 35° C., $[\alpha]_D^{24}$ + 34°(in 5N HCl) | 600 Parts |
| Water | 300 Parts |
| Sorbitol | 700 Parts |

The Gly-Trp was suspended in a mixture of the water and the sorbitol. If desired conventional amounts of flavorant and colorant is added to provide a suspension for oral administration.

EXAMPLE XI

Injectable Composition

Ala-Trp (50 Parts), were taken up in water (941 Parts) (w/w) and Sodium Chloride (3 parts) added to bring the solution to isotonicity, then to pH 5.5 through 6 by the addition of sodium hydroxide or hydrochloric acid as required and the resultant mixture filtered through a 0.1 micron membrane filter to remove all particulate matter. The filtrate was then put up in injecton ampules. Prior to utilization all components in this preparation were previously steam autoclaved.

In accordance with the above procedure Gly-Trp and other of the previously named oligopeptides may be prepared for injection.

EXAMPLE XII

Tablet Formulation-Mixed Peptides

In accordance with the procedures of Example VIII but utilizing in place of 1500 Parts Ala-Trp, 1500 of equal parts by weight of Gly-Trp and Trp, there is obtained a tableting composition which is then similarly converted into tablets for oral administration.

EXAMPLE XIII

In accordance with the procedures of Example IX, but in place of utilizing Ala-Trp, there is employed a similar amount of a 1 to 1 (by weight) mixture of Gly-Trp and Trp. There is obtained a tableting composition suitable for the manufacture of tablets for oral administration.

EXAMPLE XIV

In accordance with the procedures of Example XI, but in place of utilizing 50 Parts of Ala-Trp there is utilized 60 parts of a 5:1 (by weight) mixture of Ala-Trp and Trp to yield an injectable composition. In place of Ala-Trp there may be employed Gly-Trp or any of the other suitable oligopeptides in conjunction with Trp.

EXAMPLE XV

In accordance with the procedures of Example X, but in place of utilizing 600 Parts of Gly-Trp, there is utilized a mixture of 600 Parts of Gly-Trp and Trp (1:1 by weight) to yield a similar suspension for oral administration.

EXAMPLE XVI

Experiment on the Resorbtion of Gly-Trp in Comparison to Trp in Rats

Sprague-Dawley rats were utilized for this Experiment. The rats were fasted for 18 hours and the test substances administered through an oral stomach tube. In the Experiments both substances were tested against each other. The dosage was regulated in accordance with the body weight of the test animals. There was applied 13.3 micro moles Trp or 6.7 micro moles of Gly-Trp in 4 ml of water per 100 grams body weight. For the testing of the resorption 50 micro liters of blood were removed from the tail tip into heparinized hematocrit capillaries. The blood was taken before administration and 5, 10, 20, 30, 45, 60, 90, 120, 180 and 240 minutes after administration.

The utilization of red blood in capillaries enabled the determination of hematocrit as well as avoiding the change of blood volume due to several takings of blood.

The plasma was utilized for the examination of the blood in which 20 micro liters of blood were treated with 200 micro liters of 0.4 m perchloric acid which mixture was then immediately centrifuged. The supernatent liquid was then analysed. The material was eluted through a pair of silica gel columns containing C18 SIL-X10 gel $25 \times 0.4 + 5$ cm $\times 0.4$. Elution was with 0.5M sodium acetate/0.5 m citric acid/17% methanol at pH 4.2. Detection was by fluorometry at 276/350 mm.

The results obtained are shown on the accompanying figure. On the Figure, N is the number of rats.

We claim:

1. A method of administering to a subject an effective amount of a compound selected from the group consisting of glycyl-tryptophan and glycyl-tryptophan in conjunction with L-tryptophan, or the addition salts thereof with pharmaceutically acceptable bases or acids, to effectively treat psychological depression in said subject.

2. A method of administering to a subject an effective amount of a compound selected from the group consisting of glycyl-tryptophan and glycyl-tryptophan in conjunction with L-trp, or the addition salts thereof with pharmaceutically acceptable bases or acids, to effectively treat sleeplessness in said subject.

3. A composition for treating sleeplessness in a subject consisting essentially of, as active agent, an effective amount of a compound selected from the group consisting glycyl-tryptophan and glycyl-tryptophan in conjunction with L-tryptophan, or the addition salts thereof with pharmaceutically acceptable bases or acids and a pharmaceutically acceptable carrier.

4. A composition for treating psychological depression in a subject consisting essentially of, as active agent, an effective amount of a compound selected from the group consisting of glycyl-tryptophan and glycyl-tryptophan in conjunction with L-tryptophan, or the addition salts thereof with pharmaceutically acceptable bases or acids and a pharmaceutically acceptable carrier.

5. A method of claim 1 which comprises administering to said subject an effective amount of glycyl-tryptophan in conjunction with L-tryptophan or the addition salts thereof with pharmaceutically acceptable bases or acids.

6. A composition of claim 3 for treating sleeplessness in a subject comprising, as active agent, an effective amount of glycyl-tryptophan in conjunction with L-tryptophan or the addition salts thereof with pharmaceutically acceptable bases or acids and a pharmaceutically acceptable carrier.

7. A method of claim 2 which comprises administering an effective amount of glycyl-tryptophan in conjunction with L-tryptophan or the addition salts thereof with pharmaceutically acceptable bases or acids.

8. A composition of claim 4 for treating psychological depression in a subject comprising, as active agent, a pharmacologically effective amount of glycyl-tryptophan in conjunction with L-tryptophan or the addition salts thereof with pharmaceutically acceptable bases or acids and a pharmaceutically acceptable carrier.

* * * * *